United States Patent [19]

Sato et al.

[11] Patent Number: 4,551,568
[45] Date of Patent: Nov. 5, 1985

[54] PROCESS FOR NITRATION OF BENZENE

[75] Inventors: Hiroshi Sato, Ibaraki; Shuzo Nakamura, Takatsuki, both of Japan

[73] Assignee: Sumitomo Chemical Company, Limited, Osaka, Japan

[21] Appl. No.: 485,453

[22] Filed: Apr. 15, 1983

[30] Foreign Application Priority Data

Apr. 16, 1982 [JP] Japan .................................. 57-64202

[51] Int. Cl.$^4$ ............................................ C07C 79/10
[52] U.S. Cl. ................................... 568/939; 568/940; 260/688
[58] Field of Search ............... 568/939, 940, 937, 938, 568/939; 260/688

[56] References Cited

U.S. PATENT DOCUMENTS 2,109,873  3/1938  Wilhelm .
3,792,099  2/1974  Wang et al. ........................ 528/396
4,415,744 11/1983  Schumacher et al. .............. 568/939

FOREIGN PATENT DOCUMENTS 118539  7/1982  Japan .
866162  4/1941  United Kingdom .
586732  3/1947  United Kingdom .

OTHER PUBLICATIONS

McKee, Ind. & Eng. Chem., pp. 662–667, Jun. 1936.

Primary Examiner—John F. Terapane
Assistant Examiner—Anne Brooke
Attorney, Agent, or Firm—Cushman, Darby & Cushman

[57] ABSTRACT

Benzene is efficiently nitrated in gaseous phase with $NO_2$ or $N_2O_4$ in the presence of a catalyst of acidic mixed oxide containing two or more sorts of metal oxides, for example, $MoO_3-WO_3$, $MoO_3-TiO_2$, $WO_3-TiO_2$, $TiO_2-ZnO$ or $TiO_2-SiO_2$.

10 Claims, No Drawings

PROCESS FOR NITRATION OF BENZENE

FIELD OF THE INVENTION

The present invention relates to a process for gas phase nitration of benzene, particularly, to a process for production of nitrobenzene by gas phase nitration of benzene with $NO_2$ or $N_2O_4$. More particularly, the present invention features in the presence of metal oxide catalyst as defined below in the process mentioned above.

DESCRIPTION OF PRIOR ART

Nitrobenzene is used in large quantities as a material for aniline or an intermediate for chemicals in organic industry, and it is one of the important basic industrial chemicals. A process for producing nitrobenzene has not been changed in principle since nitration of benzene was first carried out by E. Mitscherlich in 1834. That is, benzene is nitrated in a liquid phase with a mixed acid which is a mixture of nitric acid and conc. sulfuric acid. This process, although its engineering has progressed from a batch process at the initial stage to a continuous one at the present time, there are still problems left unsolved which are peculiar to the liquid-phase process such as treatments of waste sulfuric acid and of waste water.

On the other hand, a gas-phase nitration process with $NO_x$ has been studied for its following advantages that can be expected, i.e., the process is simple, produces no waste sulfuric acid, and is able to utilize nitrogen oxide not expensive than conc. nitric acid. However, commercially-scaled production in gas-phase has not been carried out, since the process is inferior to the liquid-phase one in reaction yield and catalytic activity. There are only two literatures mentioned below, as to the gas-phase nitration of benzene.

(1) In U.S. Pat. No. 2,109,873 and Industry and Engineering Chemistry, June, 1936, pp 662, there is a description that the gas-phase nitration of benzene with $NO_2$ is carried out with silica gel as catalyst. According to this description, silica gel having particularly a large surface area is highly active, but even in such case, the space time yield stays at such a low level as about 0.0145 to about 0.0513 kg nitrobenzene/kg catalyst.hour when benzene is supplied at extremely a low feed rate, as expressed in WHSV (weight space velocity), of 0.0206 to 0.165 kg/kg catalyst.hour under a condition that the reaction temperature is as high as 310° C. and an $NO_2$/benzene molar ratio is 2.

According to the description of the same literature, it is reported that only silica gel has a catalytic activity and that bauxite, active alumina, $TiO_2$-pumice and the like have no effect on the gas-phase nitration of benzene. Also, the reaction is assumed to follow the following equation:

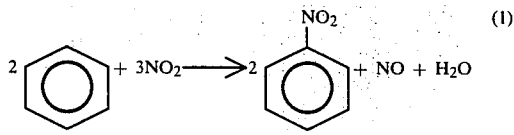

(2) British Pat. No. 586,732 discloses that the gas-phase nitration of benzene with $HNO_3$ or $NO_2$ is carried out with phosphates or a sintered product of phosphoric acid supported on a solid absorbent as catalyst. According to the example, nitrobenzene is obtained by the nitration of benzene with $HNO_3$ with calcium metaphosphate as a catalyst, but the space time yield of nitrobenzene stays at such a low level as about 0.074 kg/liter catalyst.hour under a condition that the $HNO_3$/benzene molar ratio is 0.364, the temperature is 175° C. and WHSV is 0.176 kg/liter catalyst.hour. The above literature gives no examples with $NO_2$ as a nitrating agent, so that the substantial embodiment of this invention is interpreted as nitration with nitric acid.

On the other hand, a gas-phase nitration is being studied for the purpose of controlling the ratio of nitrochlorobenzene isomers (para/ortho ratio) formed in the nitration of chlorobenzene. Japanese Patent Application Kokai (Laid-open) No. 95521/1979 discloses that, when chlorobenzene is nitrated with $NO_2$ in a gaseous phase in the presence of a molecular sieve catalyst (zeolite catalyst) having a small pore size of about 5 Å to about 10 Å, nitrochlorobenzene having an ortho/para ratio controlled in a broad range is obtained. In this case, as specific examples of the zeolite catalyst, there are given Zeolone-900H, AW-500 sieve, Zeolone 300 and 13X Molecular sieve. When for example Zeolone-900H was used as a catalyst, the following reaction result was obtained: The space time yield (STY) was 0.098 kg/liter catalyst.hour when chlorobenzene was supplied at a feed rate, as expressed in WHSV, of 0.289 kg/liter catalyst.hour (diluted with 30-fold nitrogen gas) under a condition that the reaction temperature was 200° C. and the $NO_2$/chlorobenzene molar ratio was 2.37. But the activity of this catalyst is still insufficient.

The literature described above gives no description that the gas-phase nitration of benzene was carried out using the afore-mentioned zeolite catalyst.

Further, there are known a series of similar patents to the foregoing one having an object of controlling the para/ortho ratio in the nitration of halobenzene. That is, there are given Japanese Patent Application Kokai (Laid-open) Nos. 121234/1975, 126626/1975, 126627/1975, 6931/1976 and 19734/1976. All these patents relate to the gas-phase nitration of halobenzene, but judging from the contents of description and examples in the specification, the embodiment of these inventions is substantially limited to a process with nitric acid as a nitrating agent.

In the specification of the patents described above, there is seen a description that $NO_2$ may also be used as a nitrating agent, but there are no specific examples backing the description. Also, nitric acid and $NO_2$ are clearly different from each other in chemical species because the former has nitrogen in a pentavalent oxidation state and the latter has a one in a tetravalent one. Consequently, the embodiment with nitric acid as nitrating agent and that with $NO_2$ as nitrating agent should be considered to belong to different technical systems.

These patents give only a description on the nitration of halobenzene, giving no description on the production of nitrobenzene by the nitration of benzene.

As described hereinbefore, nitrobenzene is one of the basic industrial chemicals, and its market demand far exceeds that of halonitrobenzene. A more beneficial process for producing the same is therefore expected to have immeasurably large merit.

SUMMARY OF THE INVENTION

In the light of potentiality of gas-phase nitration process of benzene with $NO_2$ or $N_2O_4$, the present invention is attained by discovering new sorts of catalysts which have not been employed for the process concerned.

That is, the present invention provides the following process: In the process for the gas-phase nitration of benzene with $NO_2$ or $N_2O_4$, a process for the gas-phase nitration of benzene characterized in that an acidic mixed oxide containing not less than two kinds of metallic oxide is used as a catalyst. According to the process of the present invention, extremely a high catalytic activity is obtained as compared with the silica gel catalysts or phosphate type ones which are used in the conventionally well-known gas-phase nitration of benzene, and besides a high reaction selectivity of avoiding producing by-product such as dinitrobenzene is realized. The liquid-phase nitration with a mixed acid comprising nitric acid and sulfuric acid is explained based on the ionic mechanism shown by the following equations (2) to (4) (Kirk-Othmer: "Encyclopedia of Chemical Technology, Vol. 13, 785–788):

$$HNO_3 + H_2SO_4 \rightleftharpoons H_2NO_3^+ + HSO_4^- \qquad (2)$$

$$H_2NO_3^+ \rightleftharpoons NO_2^+ + H_2O \qquad (3)$$

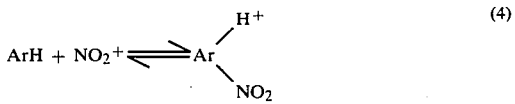
$$ArH + NO_2^+ \rightleftharpoons Ar\begin{smallmatrix}H^+\\ \diagup\\ \diagdown\\ NO_2\end{smallmatrix} \qquad (4)$$

While there are various theories for the explanation of the gas-phase nitration, either of them being not yet decisively justified. According to pages 790 to 795 in the foregoing cited literature, said gas-phase nitration is explained based on the radical mechanism shown by the following equations (5) to (7):

$$HNO_3 \rightarrow \cdot OH + \cdot NO_2 \qquad (5)$$

$$RH + \cdot NO_2 \rightarrow R\cdot + HNO_2 \qquad (6)$$

$$R\cdot + \cdot NO_2 \rightarrow RNO_2 \qquad (7)$$

But Jack E. Richmann et al assume the mechanism of reaction between an aromatic cationic radical and $NO_2$ shown by the following equations (8) and (9) [Journal of the American Chemical Society, 1981 (103), 5265-7]:

$$C_6H_6^+ \cdot + C_6H_6 \rightleftharpoons (C_6H_6)_2^+ \cdot \qquad (8)$$

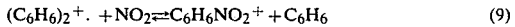
$$(C_6H_6)_2^+ \cdot + NO_2 \rightleftharpoons C_6H_6NO_2^+ + C_6H_6 \qquad (9)$$

While Autloos P et al assume a cationic mechanism [International Journal of Chemical Kinetics, 1978 (10), 657–667]. Under the situation as described so far, the search for new catalysts active to the gas-phase nitration and even conception of the working hypothesis on mechanisms were extremely difficult. It is, therefore, a really surprising discovery that the acidic mixed oxide used in the process of the present invention displays a high activity.

DETAILED DESCRIPTION OF THE INVENTION

Below, explanation will be directed to the catalyst used in the present invention. The acidic mixed oxide containing not less than two kinds of metallic oxide is one of the typical solid acid catalysts, which is described in detail, for example, in Second chapter, III part of "METALLIC OXIDES AND MIXED OXIDES" edited by Tanabe et al (published in 1978 from Kodansha Scientific). There is observed a tendency for the acidic metallic oxides used in the present invention to show that those having an acidity indicate a better activity, and mixed oxides having a strong acidity.

The first group of acidic mixed oxides to be used in the present invention is a mixed oxide system containing the oxide of Mo or W. Typical examples of this system include $MoO_3$—$WO_3$, $MoO_3$—$SiO_2$, $WO_3$—$SiO_2$, $MoO_3$—$TiO_2$, $WO_3$—$TiO_2$, $MoO_3$—$SnO_2$ and the like.

Another group of acidic mixed oxides to be used in the present invention is a mixed oxide system containing the oxide of Ti as one component. Typical examples of this system include $TiO_2$—$SiO_2$, $TiO_2$—$ZrO_2$, $TiO_2$—$SnO_2$, $TiO_2$—$CdO$, $TiO_2$—$ZnO$ and the like.

Referring to the plurality of the acidic component oxides in the present invention, ternary system or more combination system is included, in addition to the foregoing binary systems. Examples of such system are $SiO_2$—$TiO_2$—$ZrO_2$, $MoO_3$—$WO_3$—$SiO_2$ and the like.

The acidic mixed oxide systems used in the present invention mentioned above can be explained in other words as the systems containing at least one component selected from the group of $WO_3$, $MoO_3$ and $TiO_2$ as indispensable component and containing optionally one or more component selected from the group of $SiO_2$, $ZnO$, $SnO_2$, $ZrO_2$, $CdO$ and the like. Among the systems $WO_3$—$MoO_3$ is most favorable.

The mixed oxides referred to herein can be a simple mixture of the component oxides, but are in most cases, deemed to be a mixture comprising partial substitution of one element with a different one in the oxide crystal lattice, which may be considered to cause the development of acidity of the mixed oxide.

As for preparation of the mixed oxides in the present invention, the usual methods described in reference texts and literatures may be employed. For example, in the case of Ti, Si or Zn system mixed oxides, a mixed aqueous solution containing the salts of the respective metals is generally hydrolyzed with aqueous ammonia or urea to prepare the mixed oxide. In addition to these, available are a method to knead the hydroxides of metals, a method to soak the oxide of one metal in the solution of the salt of a different metal, a method to add aqueous ammonia to the soaked state, followed by calcination, and the like. While in the case of Mo or W system mixed oxides, available are a method to mix $WO_3$ and $MoO_3$ in a dry or wet state, a method to add the isopropanol solution of titanium tetraisopropoxide to an aqueous ammonium molybdate solution to coprecipitate the hydroxides, a method to soak silica gel in an aqueous ammonium tungstate solution, followed by concentration, and the like. Any of these methods will provide the aimed mixed oxide from which catalyst is normally obtained by calcining mixture at 400° to 600° C. for several hours in an air stream.

In the case of the mixed oxide catalyst, it is well known to those skilled in the art that the catalytic activity varies with the preparative condition, calcining temperature and the like, which holds true of the gas-phase nitration in the present invention. Consequently, in the case of the foregoing mixed oxide catalyst used in the present invention, the preparative method should also closely be controlled, and the work conditions should be firmly set up so as to obtain an optimum activity of each catalyst system. For setting up the condition mentioned above, one control measure or region is recommended in which the mixed oxide obtained develops acidity, as expressed in the acid strength function (Ho), of Ho≦3, preferably Ho≦+1.5. The definition and measurement of the acid strength function, Ho, is furnished by a detailed description at pages 73 to 76 and 161 of Tanabe et al. "ACID AND BASE CATALYSTS" (published in Showa 41st year from Sangyo Tosho Co.). In a practice of the present invention, the development method with indicators is also employed for Ho measurement. But it is to be noted that the value of Ho≦3 or Ho≦+1.5 as given above, deserves a handy measure as one control method for the foregoing catalyst preparation, and therefore when color development with indicators is difficult to confirm with colored mixed oxides (e.g. $MoO_3$—$WO_3$ system), it should be substituted by the adsorption/desorption method or the like. The $MoO_3$—$WO_3$ mixed oxide is an example of those which have a high activity in the gas-phase nitration and are very difficult to determine their accurate Ho value (the acidity of $MoO_3$—$WO_3$ generally ranges +3.0≧Ho≧+1.5), nevertheless those are included in the present invention.

The nitrating agent in the process of the present invention includes $NO_2$, $N_2O_4$ and the like, of which $NO_2$ is particularly preferred. It is well known that NO is rapidly oxidized into $NO_2$ in the coexistence of oxygen, and also in the present invention, a process may be employed in which a mixed gas of NO and $O_2$ is fed and $NO_2$ formed in the reaction system is used as nitrating agent.

The gas-phase nitration in the present invention is carried out by continuous feeding a gaseous mixture of benzene and a nitrating agent onto the acidic mixed oxide catalyst bed while maintaining the reaction temperature at 80° to 250° C., and separating the formed nitrobenzene from the foregoing gaseous mixture. Preferably, said gas-phase nitration is carried out in the coexistence of an inert gas such as nitrogen which is a diluent. Below, a specific embodiment to indicate how to carry out the reaction will be given.

Benzene is vaporized by pre-heating, and after mixing with a diluent nitrogen gas of a definite flow rate, fed to a reactor. Thereafter, before contact with the heated catalyst bed, the gaseous mixture is mixed with the gaseous flow of a nitrating agent (e.g. $NO_2$) and introduced into the heated catalyst bed wherein catalytic reaction is carried out.

A nitrating agent preferably used in the present invention is $NO_2$, and an $NO_2$/benzene molar ratio is generally 0.1 to 3.0, further preferably 0.1 to 2.0.

Each reaction component and a diluent nitrogen gas may be fed to a reactor at an optional space velocity while they are maintained at a predetermined composition ratio.

PREFERRED EMBODIMENTS OF THE INVENTION

In order to explain the present invention in more detail, specific examples will be given below. In these examples, the activity of catalyst is compared and examined by two methods. One method is a normal pressure fixed bed flow reaction commonly used to test the catalytic activity, and the other is a micropulse reaction. The first method, a normal pressure fixed bed flow reaction, has been frequently used, as one of indicating the so-called stationary activity, to demonstrate the catalytic activity in many patents, literatures and the like. Consequently no problem is seen in using the first method. The second method, a micropulse reaction, used in the present invention, uses a reactor, that is to say, a microreactor is directly connected with a gas chromatography. This method is very simple to measure the catalytic activity, but the value obtained is said to indicate the so-called non-stationary activity. As to the micropulse reaction, Murakami et al. [Catalyst, Vol. 23(6), 483–487, 1981] and Walter T. Reichle (CHEMTECH, Nov. 1981, 698–702) offer reference information about the usefulness and precautions thereof in the catalytic activity test. According to their description, the results of the both methods sometimes agree or disagree with each other since the micropulse reaction is concerned with a non-stationary reaction and the flow reaction is a stationary reaction as described hereinbefore. Apart from a detailed comparison of the reactions, the both methods sufficiently stand use in the rough comparison of activity as to whether or not the activity of a certain catalyst is zero, or to know if a large difference in activity is present between two catalysts. In fact, examples based on the use of micropulse reaction for the comparison of catalytic activity are also found in various literatures [for example, rough draughts (A) for the 48th Catalyst Discussion Meeting (1981), pp 194, 220, 236, 272, 278].

In the present invention, the micropulse reaction method is used for its simplicity, also properly collected are data for comparison with the normal pressure flow reaction method. As a result, it is confirmed that, referring to specific reaction conditions (gas-phase nitration of benzene with $NO_2$ for the present invention), the tendency observed with respect to the magnitude of catalytic activity by the micropulse reaction agrees with that by the normal pressure flow reaction.

Examples given below are part of the specific embodiments of the present invention, which is not however to be interpreted as being limited to these examples.

The conversion, yield and selectivity in the examples are calculated as follows:

$$\text{Conversion of benzene} = \frac{\text{Raw stock benzene} - \text{Unreacted benzene}}{\text{Raw stock benzene}} \times 100 \, (\%)$$

$$\text{Yield of nitrobenzene} = \frac{\text{Formed nitrobenzene (mole)}}{\text{Raw stock benzene (mole)}} \times 100 \, (\%)$$

$$\text{Selectivity of nitrobenzene} = \frac{\text{Yield of nitrobenzene}}{\text{Conversion of benzene}} \times 100 \, (\%)$$

EXAMPLE 1

(Catalytic activity test by micropulse reaction)

The micropulse reaction method will first be explained. The reaction apparatus is described in detail in the literature of Murakami et al cited above [Catalyst, Vol. 23(6), 483–487, 1981]. A quartz glass microreactor, 4 mm in inside diameter and 20 cm in length, is placed in an electric furnace and mounted on the forestage of the injection part of a gas chromatograph. Quartz wool is packed in the microreactor to make a vaporizer, and about 50 mg to about 200 mg of a catalyst is packed below the vaporizer. The catalyst layer is first preheat-treated at a predetermined temperature while passing a definite flow amount of nitrogen or helium, a carrier gas, through the reactor. Thereafter, about 0.5 to 1 μliter of a benzene/$N_2O_4$ mixture in ice cooling (since there are no data of inflammability limit for such benzene/$N_2O_4$ mixture, latent danger may be thought of, and therefore the smallest possible amount of the mixture was prepared and treated under ice cooling) is sampled rapidly by means of a microsyringe and injected into the microreactor at the upper part thereof. The benzene/$N_2O_4$ mixture passes through the quartz wool-packed vaporizer together with the carrier gas (nitrogen or helium), and after turning benzene vapor and $NO_2$, respectively, comes into contact with the catalyst bed to react. This reaction mixture is directly introduced into the gas chromatograph and analyzed.

Experiment was carried out as follows using the foregoing micropulse reactor.

Five grams of molybdenum oxide and 15 g of tungsten oxide were mixed in a mortar and pressure-molded with addition of 2.25 g of water. The molded product was pulverized to a particle size of 24 to 48 mesh and calcined at 500° C. for 3 hours in an air stream to obtain a $MoO_3$—$WO_3$ mixed oxide. The composition of this oxide was Mo/W=1/1.87 (atomic ratio). Thereafter, 50 mg of the $MoO_3$—$WO_3$ mixed oxide (after pressure-molded and pulverized to a particle size of 24 to 48 mesh) was packed in the microreactor and preheat-treated at 400° C. for 0.5 hour while passing helium therethrough at a flow rate of 48 ml/minute. Thereafter, 0.5 μliter of a benzene/$N_2O_4$ mixture ($NO_2$/benzene molar ratio=2.7) in ice cooling was sampled by means of a microsyringe and rapidly injected into the microreactor at the upper part thereof. The temperature of the catalyst bed (reaction temperature) was 200° C. Analytical conditions on the gas chromatograph were as follows:

Glass column: 3φ×2 m
Column packing: 5% PEG 20M/Uniport HP 60-80 mesh
Temperature of injection part: 250° C.

Temperature of column: 80° C. (8 minutes) $\xrightarrow[\text{temperature-rise}]{4° \text{C./minute}}$ 160° C.

The result obtained: Conversion of benzene, 43.3%; and selectivity of nitrobenzene, 99.9%.

EXAMPLE 2

A hydrogel, as obtained by the coprecipitation method in which an isopropanol solution of titanium tetraisopropoxide is added dropwise to an aqueous ammonium molybdate solution, was filtered, dried and calcined at 500° C. for 6 hours in an air stream to obtain a $MoO_3$—$TiO_2$ mixed oxide. The composition ratio of this oxide was Mo/Ti=1/9 (atomic ratio). Thereafter, experiment was carried out in completely the same manner as in Example 1 except that 50 mg of this $MoO_3$—$TiO_2$ mixed oxide was used as catalyst.

The result obtained: Conversion of benzene, 53.2%; and selectivity of nitrobenzene, 98.5%.

EXAMPLE 3

A $WO_3$—$TiO_2$ mixed oxide was prepared according to Example 2 from an aqueous ammonium tungstate solution and an isopropanol solution of titanium tetraisopropoxide. The composition ratio was W/Ti=1/9 (atomic ratio). The $WO_3$—$TiO_2$ mixed oxide obtained developed a slight acidic color with a dicinnamal acetone indicator, showing that it has an acidity of Ho≦−3.0. Experiment was carried out in completely the same manner as in Example 1 except that 50 mg of this $WO_3$—$TiO_2$ mixed oxide was used as catalyst.

The result obtained: Conversion of benzene, 26.5%; and selectivity of nitrobenzene, 99.3%.

EXAMPLE 4

3.8 g of titanium tetrachloride was added dropwise to 100 ml of distilled water, and 4.16 g of tetraethyl orthosilicate was then added dropwise thereto. This uniform solution was neutralized (ph=7) with dropwise addition of a 28% aqueous ammonia to deposit a hydrogel by the coprecipitation method. The hydrogel was aged for 1 hour on a water bath, filtered, washed and dried at 100° C. for 20 hours. The dried product was calcined at 500° C. for 3 hours in an air stream to obtain a $TiO_2$—$SiO_2$ mixed oxide. The composition of this oxide was Ti/Si=1/1 (atomic ratio). The $TiO_2$—$SiO_2$ mixed oxide obtained developed a slight acidic color with a dicinnamal acetone indicator, showing that it has an acidity of Ho≦−3.0. Experiment was then carried out in completely the same manner as in Example 1 except that 50 mg of this $TiO_2$—$SiO_2$ mixed oxide was used as catalyst and that an $NO_2$/benzene molar ratio was 1.0.

The result obtained: Conversion of benzene, 14.6%; and selectivity of nitrobenzene, 98.3%.

CONTROL EXAMPLE 1

Reaction was carried out according to Example 1 except that 50 mg of silica gel, a well-known catalyst for gas-phase nitration from benzene/$NO_2$ (U.S. Pat. No. 2,109,873) was used, and besides that the predetermined reaction temperatures shown in Table 1 were used (provided that an $NO_2$/benzene molar ratio was 2.4). The results obtained are shown in Table 1.

TABLE 1

| Reaction No. | Catalyst (silica gel) | Reaction temperature (°C.) | Conversion of benzene (%) | Selectivity of nitrobenzene (%) |
|---|---|---|---|---|
| 1 | $SiO_2$ (product of Dokai Kagaku Co.; surface area, 720 m²/g) | 300 | 6.9 | 96.7 |
| 2 | $SiO_2$ (product of Dokai Kagaku Co.; surface area, 720 m²/g) | 200 | 6.0 | 99.6 |
| 3 | $SiO_2$ (product of Nikki Kagaku Co.; Lot No. N-608) | 300 | 3.4 | 98.1 |
| 4 | $SiO_2$ (product of Nikki Kagaku Co.; Lot No. N-608) | 200 | 1.9 | 99.6 |

EXAMPLE 5

Experiment was carried out as follows using the usual apparatus for normal pressure fixed bed flow reaction. Five grams (1.8 cc) of the $MoO_3$—$WO_3$ mixed oxide catalyst prepared in Example 1 (Mo/W atomic ratio=1/1.87) (24 to 48 mesh) was packed in a quartz glass reactor of 32 cm in length and 1 cm in inside diameter, and preheat-treated at 400° C. for 1 hour in a nitrogen stream. Benzene was fed to the molten alumina-packed vaporizer by means of a micro-feeder to vaporize. While $N_2O_4$ was fed by means of an ice-cooled micro-feeder, and the vaporized $NO_2$ was diluted with a diluent nitrogen carrier gas and then mixed with the benzene vapor. The mixed gas, a starting material, was introduced into the reactor whereby catalytic reaction was carried out at the catalyst bed kept at a predetermined temperature. The gaseous reaction mixture, after leaving the reactor, was trapped under ice-cooling, and the waste gas was neutralized with an aqueous alkali liquor and purged. The trapped product was analyzed by gas chromatography. The reaction result in each reaction condition is shown in Table 2, provided that the abbreviations in the table are as follows:
SV: Gas space velocity ($hr^{-1}$)
STY: Space time yield (kg/liter cat.·hr)

EXAMPLE 7

According to the catalyst preparation method in Example 1, a $MoO_3$—$WO_3$ mixed oxide catalyst was prepared ($MoO_3=5$ wt. %). Calcination was carried out at 500° C. for 3 hours in an air stream.

The catalyst obtained was made of a uniform particle size of 24 to 48 mesh, and 5 ml of this catalyst was packed in a quarts reactor. Reaction was then carried out according to Example 5, provided that the feed rate of benzene was kept constant at 6.16 g/hr and the $NO_2$/benzene molar ratio was varied by varying the feed rate of $NO_2$. The balance of SV was controlled with $N_2$, a diluent. Every run showed a stationary activity value 6 hours after the beginning of feed. The results obtained are shown in Table 4.

TABLE 2

| No. | Passage of time (hr) | Feed condition | | | | | Reaction temperature (°C.) | Conversion of benzene (%) | Yield of nitrobenzene (%) | Selectivity of nitrobenzene (%) | STY of nitrobenzene (kg/liter cat.·hr) |
| | | Benzene (g/hr) | $NO_2$ (g/hr) | $NO_2$/benzene (molar ratio) | $N_2$ (cc/min) | SV ($hr^{-1}$) | | | | | |
|---|---|---|---|---|---|---|---|---|---|---|---|
| 1 | 1.25 | 1.99 | 2.75 | 2.34 | 375 | 13,560 | 200 | 31.48 | 27.6 | 87.7 | 0.481 |
| 2 | 7.25 | " | " | " | " | " | " | 31.0 | 25.9 | 83.4 | 0.452 |
| 3 | 10.0 | " | " | " | " | " | " | 34.5 | 28.5 | 82.6 | 0.497 |
| 4 | 17.75 | 2.73 | 1.69 | 1.05 | 100 | 4,090 | 150 | 15.6 | 15.1 | 96.8 | 0.361 |
| 5 | 20.0 | " | " | " | " | " | " | 16.1 | 16.1 | 100 | 0.385 |

TABLE 4

Common reaction condition:
Catalyst = 5.0 ml, reaction temperature = 150° C., benzene = 6.16 g/hr, $NO_2$/benzene molar ratio was varied, $N_2$ = 3 liter/hr, SV = 1100 $hr^{-1}$

| Run No. | $NO_2$/benzene (molar ratio) | Passage of time (hr) | Conversion of benzene (%) | Yield of nitrobenzene (%) | Selectivity of nitrobenzene (%) | STY of nitrobenzene (kg/liter cat.·hr) |
|---|---|---|---|---|---|---|
| 1 | 0.085 | 6.0 | 2.22 | 2.2 | >99 | 0.0427 |
| 2 | 0.20 | " | 4.79 | 4.75 | " | 0.0923 |
| 3 | 0.37 | " | 9.59 | 9.5 | " | 0.185 |
| 4 | 0.58 | " | 15.2 | 15.0 | " | 0.291 |

EXAMPLE 6

According to the catalyst preparation method in Example 1, $MoO_3$—$WO_3$ mixed oxide catalysts having varying mixing ratios were prepared by the kneading method. Calcination was carried out at 500° C. for 3 hours in an air stream. The catalysts obtained were made of a uniform particle size of 24 to 48 mesh, and 4.6 ml of each catalyst was packed in a quarts reactor. Reaction was then carried out according to Example 5. Every run showed a stationary activity value six hours after the beginning of feed. The results obtained are shown in Table 3.

EXAMPLE 8

A $MoO_3$—$WO_3$ mixed oxide catalyst containing 5 wt. % of $MoO_3$ was prepared in the same manner as in Example 7. After the oxide was made of a uniform particle size of 24 to 48 mesh, it was calcined at 500° C. for 3 hours in an air stream, and 5 ml of the catalyst obtained was packed in a quartz reactor. Reaction was then carried out according to Example 5, provided that the reaction temperature was varied as shown in Table 5. Every run showed a stationary activity value 6 hours after the beginning of feed. The results obtained are shown in Table 5.

TABLE 3

Common reaction condition:
Catalyst = 4.6 ml, reaction temperature = 150° C., benzene = 6.05 g/hr, $NO_2$/benzene/$N_2$ = 1/1/3.45 (molar ratio), SV = 2,000 $hr^{-1}$

| Run No. | Catalyst composition $\frac{MoO_3}{MoO_3 + WO_3}$ (wt. %) | Passage of time (hr) | Conversion of benzene (%) | Yield of nitrobenzene (%) | Selectivity of nitrobenzene (%) | STY of nitrobenzene (kg/liter cat.·hr) |
|---|---|---|---|---|---|---|
| 1 | 0 | 6.0 | 6.16 | 6.1 | >99 | 0.126 |
| 2 | 2.5 | " | 19.7 | 19.5 | " | 0.405 |
| 3 | 5.0 | " | 24.2 | 24.0 | " | 0.498 |
| 4 | 10.0 | " | 20.7 | 20.5 | " | 0.425 |
| 5 | 25.0 | " | 18.2 | 18.0 | " | 0.373 |

TABLE 5

Common condition:
Catalyst = 5 ml, benzene = 6.16 g/hr. $NO_2$/benzene/$N_2$ = 0.2/1.0/0.15 (molar ratio),
SV = 500 $hr^{-1}$

| Run No. | Reaction temperature (°C.) | Passage of time (hr) | Conversion of benzene (%) | Yield of nitrobenzene (%) | Selectivity of nitrobenzene (%) | STY of nitrobenzene (kg/liter cat · hr) |
|---|---|---|---|---|---|---|
| 1 | 85  | 6.0 | 3.0  | 3.0  | >99 | 0.0582 |
| 2 | 100 | "   | 4.79 | 4.75 | "   | 0.0923 |
| 3 | 120 | "   | 6.87 | 6.8  | "   | 0.132  |
| 4 | 150 | "   | 6.36 | 6.3  | "   | 0.122  |
| 5 | 200 | "   | 4.95 | 4.9  | "   | 0.095  |
| 6 | 250 | "   | 1.41 | 1.4  | "   | 0.027  |

EXAMPLE 9

A $MoO_3$—$WO_3$ mixed oxide catalyst containing 5 wt. % of $MoO_3$ was prepared in the same manner as in Example 7. After the oxide was made of a uniform particle size of 24 to 48 mesh, a predetermined amount of the oxide was packed in a quartz reactor and calcined at 500° C. for 3 hours in an air stream. Reaction was then carried out according to Example 5. Every run showed a stationary activity value 6 hours after the beginning of feed. The results obtained are shown in Table 6.

TABLE 6

Common reaction condition:
Benzene = 6.16 g/hr, $NO_2$/benzene/$N_2$ = 0.2/1/0.68 (molar ratio),
reaction temperature = 150° C.

| Run No. | Amount of catalyst (ml) | SV ($hr^{-1}$) | Passage of time (hr) | Conversion of benzene (%) | Yield of nitrobenzene (%) | Yield of* nitrobenzene based on $NO_2$ (%) | Selectivity of nitrobenzene (%) | STY of nitrobenzene (kg/liter cat · hr) |
|---|---|---|---|---|---|---|---|---|
| 1 | 5    | 470 | 12.5 | 6.82  | 6.8  | 33.1 | >99 | 0.129 |
| 2 | 10   | 331 | "    | 8.83  | 8.8  | 46.6 | "   | 0.091 |
| 3 | 23.5 | 141 | "    | 12.35 | 12.3 | 59.6 | "   | 0.049 |
| 4 | 35.1 | 94  | "    | 13.34 | 13.3 | 63.4 | "   | 0.035 |

*Yield of formed nitrobenzene based on fed $NO_2$ (mole) = $\frac{\text{Formed nitrobenzene (mole)}}{\text{Fed } NO_2 \text{ (mole)}} \times 100\ (\%)$

EXAMPLE 10

$WO_3$—$TiO_2$ mixed oxide was prepared according to Example 3, from ammonium methatungstate and titan tetraisopropoxide. The composition ratio was W/Ti=9/1 (atomic ratio). Calcination was conducted at 500° C. under air flow for 3 hours. The catalyst obtained was arranged to have a uniform particle size of 24–48 mesh.

In a quartz-made reaction column packed with 15 ml of the thus prepared catalyst, a reaction was conducted according to Example 5. The operating conditions and results are shown in the Table 7 below.

EXAMPLE 11

7.6 Ml of conc. hydrochloride was added to an aqueous solution prepared by dissolving 14.0 g of zinc chloride in 30 ml of water, then was added further an aqueous solution prepared by dissolving 398 g of ammonium sulfate in 600 ml of water thereto. The thus prepared aqueous solution containing zinc chloride was added and mixed with an aqueous solution prepared otherwise by dissolving 276 g of titanium tetrachloride in 306 ml of water.

After the mixed solution was heated on a water bath for 1 hour, it was neutralized with ammonia water and precipitation deposited was recovered by filtration and washed with water. The precipitation was dried at 120° C. overnight, then calcined at 500° C. for 3 hours to obtain catalyst, which was composed of $TiO_2$ (93 wt. %) and ZnO (7 wt. %). This catalyst was arranged to have uniform particle size of 24–48 mesh and 15 ml thereof was packed in a quartz-made reactor. The reaction was operated according to Example 5. The Table 7 shows reaction conditions and results therefrom.

TABLE 7

Common operating condition:
Benzene = 6.10 g/hr, $NO_2$/benzene/$N_2$ = 0.2/1/0.68 (molar ratio),
Reaction Temp. = 150° C., Amount of catalyst = 15 ml

| Example No. | Catalyst | SV ($hr^{-1}$) | Passage of time (hr) | Conversion of benzene (%) | Yield of nitrobenzene (%) | Yield of nitrobenzene based on $NO_2$ (%) | Selectivity of nitrobenzene (%) |
|---|---|---|---|---|---|---|---|
| 10 | $TiO_2$—$WO_3$ (1:9 molar ratio) | 222 | 3.0 | 2.9 | 2.9 | 14.5 | ≧99 |
| 11 | $TiO_2$—ZnO (93:7 weight | 222 | 8.0 | 3.6 | 3.6 | 18 | ≧99 |

TABLE 7-continued

Common operating condition:
Benzene = 6.10 g/hr, NO$_2$/benzene/N$_2$ = 0.2/1/0.68 (molar ratio),
Reaction Temp. = 150° C., Amount of catalyst = 15 ml

| Example No. | Catalyst (ratio) | SV (hr$^{-1}$) | Passage of time (hr) | Conversion of benzene (%) | Yield of nitro-benzene (%) | Yield of nitro-benzene based on NO$_2$ (%) | Selectivity of nitro-benzene (%) |
|---|---|---|---|---|---|---|---|

We claim:

1. A gas-phase nitration process of benzene with a nitrating agent of NO$_2$ or N$_2$O$_4$, which consists essentially of carrying out the process in the presence of a catalyst composed of an acidic mixed oxide consisting of at least one component selected from the group of WO$_3$, MoO$_3$ and TiO$_2$ as indispensable component and containing optionally SiO$_2$ and/or ZnO, the sole components of the mixed oxide being selected from the group consisting of WO$_3$, MoO$_3$, TiO$_2$, SiO$_2$, and ZnO.

2. A process according to claim 1, wherein the catalyst is MoO$_3$—WO$_3$, MoO$_3$—TiO$_2$, WO$_3$—TiO$_2$, TiO$_2$—ZnO or TiO$_2$—SiO$_2$.

3. A process according to claim 1, wherein the catalyst is MoO$_3$—WO$_3$.

4. A process according to claim 1, wherein said gas-phase nitration is carried out at a temperature within the range of 80° to 250° C.

5. A process according to claim 1, wherein the nitrating agent of 0.1 to 3 moles per mole of benzene is used.

6. A process according to claim 1, wherein said gas-phase nitration is carried out in the presence of a diluent comprising an inert gas.

7. A process according to claim 1, wherein the product obtained by said gas-phase nitration is nitrobenzene.

8. A process according to claim 1, wherein the process is carried out by feeding a mixture gas of NO and O$_2$ into a reaction zone.

9. A process according to claim 1, wherein the process is carried out by a normal pressure fixed bed flow reaction or a micropulse reaction system.

10. A process according to claim 1 which consists of nitrating benzene with a nitrating agent which is NO$_2$ or N$_2$O$_4$, said process consisting of carrying out the nitration with NO$_2$ or N$_2$O$_4$ alone or together with a mixture of NO and O$_2$ to form the nitrating agent in situ or in the presence of an inert gas diluent in the presence of a catalyst consisting of an acidic mixed oxide containing at least one component selected from the group consisting of WO$_3$, MoO$_3$ and TiO$_2$ as indispensable component and optionally containing SiO$_2$ and/or ZnO, the sole components of the mixed oxide being selected from the group consisting of WO$_3$, MoO$_3$, TiO$_2$, SiO$_2$, and ZnO.

* * * * *